United States Patent
Lee et al.

(10) Patent No.: US 10,136,663 B2
(45) Date of Patent: Nov. 27, 2018

(54) CURCUMINOID-BASED COMPOUND/STEVIOSIDE-CONTAINING COMPLEX FOR THE PREVENTION AND TREATMENT OF AN INFLUENZA VIRUS INFECTION

(75) Inventors: Woo-Song Lee, Daejeon (KR);
Young-Bae Ryu, Daejeon (KR);
Young-Min Kim, Daejeon (KR);
Su-Jin Park, Daejeon (KR);
Mun-Chual Rho, Daejeon (KR);
Hyung-Jae Jeong, Daejeon (KR);
Hyung-Jun Kwon, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 668 days.

(21) Appl. No.: 14/126,106

(22) PCT Filed: Jun. 13, 2012

(86) PCT No.: PCT/KR2012/004672
§ 371 (c)(1),
(2), (4) Date: May 19, 2014

(87) PCT Pub. No.: WO2012/173392
PCT Pub. Date: Dec. 20, 2012

(65) Prior Publication Data
US 2014/0248382 A1    Sep. 4, 2014

(30) Foreign Application Priority Data

Jun. 13, 2011    (KR) .................. 10-2011-0057139

(51) Int. Cl.
| | | |
|---|---|---|
| A61K 36/00 | (2006.01) |
| A61K 36/906 | (2006.01) |
| A61K 36/28 | (2006.01) |
| A23L 1/30 | (2006.01) |
| A61K 31/12 | (2006.01) |
| A61K 31/704 | (2006.01) |
| A61K 36/9066 | (2006.01) |
| A23K 20/111 | (2016.01) |
| A23K 20/163 | (2016.01) |
| A23K 50/10 | (2016.01) |
| A23K 50/75 | (2016.01) |
| A23K 50/30 | (2016.01) |
| A23L 33/105 | (2016.01) |
| A61K 47/69 | (2017.01) |

(52) U.S. Cl.
CPC ........... *A23L 1/3002* (2013.01); *A23K 20/111* (2016.05); *A23K 20/163* (2016.05); *A23K 50/10* (2016.05); *A23K 50/30* (2016.05); *A23K 50/75* (2016.05); *A23L 33/105* (2016.08); *A61K 31/12* (2013.01); *A61K 31/704* (2013.01); *A61K 36/28* (2013.01); *A61K 36/9066* (2013.01); *A61K 47/6921* (2017.08)

(58) Field of Classification Search
None
See application file for complete search history.

(56) References Cited

U.S. PATENT DOCUMENTS

2012/0107429 A1    5/2012 Lee et al.

FOREIGN PATENT DOCUMENTS

| JP | 2006-008594 A | 1/2006 |
| JP | 2006008594 A * | 1/2006 |
| JP | 2008-280333 A | 11/2008 |
| KR | 962334 B1 * | 6/2010 |
| KR | 2011-0004763 A | 1/2011 |

OTHER PUBLICATIONS

KR-10-2011-0004763A (Korea Research Institute of Bioscience and Biotechnology, Jan. 14, 2011 pp. 1-5, see English translation).*
International Search Report for Application No. PCT/KR2012/004672, dated Jan. 2, 2013. (7 pages).
Mandal et al., Microwave assisted extraction of curcumin by sample-solvent dual heating mechanism using Taguchi L9 orthogonal design. J Pharma Biomed Anal. 2008;46:322-7. Epub Oct. 23, 2007.
Wakte et al., Optimization of microwave, ultra-sonic and supercritical carbon dioxide assisted extraction techniques for curcumin from Curcuma longa. Sep Pur Technol. May 19, 2011;79:50-55.

* cited by examiner

*Primary Examiner* — Christopher R Tate
*Assistant Examiner* — Randall Winston
(74) *Attorney, Agent, or Firm* — Womble Bond Dickinson (US) LLP; John J. Penny

(57) ABSTRACT

The present invention relates to a complex comprising a compound of formula (I), or a plant extract comprising the compound or a fraction thereof; and stevioside, or a plant extract comprising the stevioside or a fraction thereof, and relates to a pharmaceutical composition for preventing or treating an influenza virus infection comprising the complex as an active ingredient. Also, the present invention relates to a food composition for preventing or improving an influenza virus infection, a virucidal quasi-drug composition, a virucidal feed additive, and a feed, which comprises the complex as an active ingredient. According to the present invention, the complex comprising a compound of formula (I), or a plant extract comprising the compound or a fraction thereof; and stevioside, or a plant extract comprising the stevioside or a fraction thereof exhibits a virucidal effect and an effect of inhibiting cell degradation against an influenza virus as well as antiviral efficacy in a specific pathogen-free (SPF) chicken, and thus can be usefully used in the prevention and treatment of an influenza virus infection.

5 Claims, No Drawings

CURCUMINOID-BASED COMPOUND/STEVIOSIDE-CONTAINING COMPLEX FOR THE PREVENTION AND TREATMENT OF AN INFLUENZA VIRUS INFECTION

TECHNICAL FIELD

The present invention relates to a complex comprising a compound of formula (I), or a plant extract comprising the compound or a fraction thereof; and stevioside, or a plant extract comprising the stevioside or a fraction thereof, and relates to a pharmaceutical composition for preventing or treating an influenza virus infection comprising the complex as an active ingredient. Also, the present invention relates to a food composition for preventing or improving an influenza virus infection, a virucidal quasi-drug composition, a virucidal feed additive, and a feed, which comprises the complex as an active ingredient.

BACKGROUND ART

Influenza virus is one of the most infective viruses that cause acute respiratory diseases, and in severe instances, cause herd infection or pandemic over the world, particularly giving rise to serious respiratory symptoms in children, the aged, patients with cardiopulmonary diseases, and the like (see Hien, T. T. et al. *N. Eng. J. Med.*, 350, 1179, 2004). Influenza virus is a genus of the Orthomyxovirus and has three types, that is, A, B, and C. Among them, particularly A and B types routinely spread in people.

Virus surface antigens produce an antigenic variation by their same subtype to generate new antigenic variants every year. Particularly, among influenza viruses, avian influenza virus, which is still a threat, undergoes an antigenic shift to infect various kinds of birds such as chickens, turkeys, ducks, wild birds, and the like. Avian influenza virus spreads so quickly that once a chicken is infected, 80% or more of the chickens are killed. Avian influenza virus which poses the most damage and threat to the poultry industry over the world causes viral diseases, and this pervasive effect is not just limited to the poultry industry. It has been reported that avian influenza virus can infect humans, which causes diseases to spread among humans (see Gubareva, L. V. et al. *Lancet.* 355, 2000).

In order to prevent and treat the influenza virus infection, consideration may be made to inhibit the absorption in epithelial cells, the invasion into cells, the transcription or replication of genes, the synthesis of proteins, or the release from cells, each having been the focus of the antiviral studies.

To treat diseases caused by influenza virus, four substances, that is, Amatadine, Rimatadine, Zanamivir, and Oseltamivir have been used with the approval of the Food and Drug Administration (FDA). Among these, Amatadine and Rimatadine are M2 inhibitors, which have antiviral effects by blocking an ion channel of a membrane protein, particularly M2 protein that is essential to the proliferation of virus, and inhibiting the uncoating of the virus, but they are only effective against influenza A virus. Also, it is reported that some viral become more tolerant and resistant to the inhibitors as a consequence of being used over 40 years, and severe side effects occur in the nervous system and stomach (see Bantia, S. et al. *Antiviral Research* 69, 39, 2006). Since 1999, as new drugs for treating virus infection, Zanamivir and Oseltamivir have been used, which play an important role in proliferation of virus, have a low prevalence of tolerance, and inhibit neuraminidases being stably present in both influenza A and B viruses (see Zhang, J. et al. *Bioorg. Med. Chem. Lett.* 16, 3009, 2006).

However, Zanamivir has an advantage of high antiviral effects but is disadvantageous in low bioavailability and quick release from the kidney (see Ryan, D. M. et al. *Antimicrob. Agents Chemother.,* 39, 2583, 1995), and Oseltamivir causes severe vomiting.

As mentioned above, the known antiviral agents have serious side effects and require considerable caution in their application. Also, the development effects of vaccines are low when the vaccine virus is not matched to circulating viruses. Accordingly, there is an increasing need for a new influenza antiviral agent with excellent infection inhibition and stability. Also, there is a need to develop a new substance exhibiting good antiviral effects in the whole animal for the substantial treatment of animals infected with an influenza virus.

The present inventors have endeavored to satisfy such a need and found that a complex comprising a curcuminoid-based compound, or a plant extract comprising the compound or a fraction thereof; and stevioside, or a plant extract comprising the stevioside or a fraction thereof has a very superior virucidal effect and an excellent effect of inhibiting cell degeneration against an influenza virus, and can effectively treat a subject infected with an influenza virus even by just a small amount.

DISCLOSURE

Technical Problem

It is an object of the present invention to provide a complex comprising a compound of formula (I), or a plant extract comprising the compound or a fraction thereof; and stevioside, or a plant extract comprising the stevioside or a fraction thereof.

It is another object of the present invention to provide a pharmaceutical composition for preventing and treating an influenza virus infection, which can exhibit an antiviral effect on the whole body of an individual infected with an influenza virus even by just a small amount, and a method of treating an influenza virus infection by administering the pharmaceutical composition to an individual.

It is yet another object of the present invention to provide a food composition for preventing or improving an influenza virus infection and a virucidal quasi-drug composition, which can exhibit an antiviral effect on the whole body of an individual infected with an influenza virus even by just a small amount.

It is still another object of the present invention to provide a feed additive for preventing or improving an influenza virus infection or for virucidal use, which can exhibit an antiviral effect on the whole body of an individual infected with an influenza virus even by just a small amount, and a feed comprising the feed additive.

Technical Solution

In order to achieve the above objects, in accordance with an aspect of the present invention, a complex comprising a compound of formula (I), or a plant extract comprising the compound or a fraction thereof; and stevioside, or a plant extract comprising the stevioside or a fraction thereof is provided:

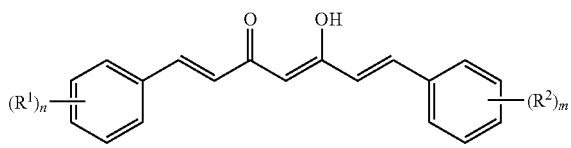

(I)

wherein, $R^1$ and $R^2$ are each independently hydrogen, hydroxy, or $C_1$-$C_{10}$ alkoxy;
n is an integer of 1 to 5; and
m is an integer of 1 to 5.

In accordance with another aspect of the present invention, there is provided a pharmaceutical composition for preventing and treating an influenza virus infection, comprising the complex as an active ingredient.

In accordance with yet another aspect of the present invention, there is provided a food composition for preventing or improving an influenza virus infection and a virucidal quasi-drug composition, comprising the complex as an active ingredient.

In accordance with still another aspect of the present invention, there is provided a feed additive for preventing or improving an influenza virus infection or for virucidal use, comprising the complex as an active ingredient, and a feed comprising the feed additive.

In accordance with still another aspect of the present invention, there is provided a method of treating an influenza virus infection, comprising administering to an individual a mixture of a compound of formula (I), or a plant extract comprising the compound or a fraction thereof; and stevioside, or a plant extract comprising the stevioside or a fraction thereof:

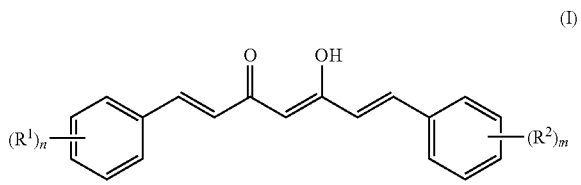

(I)

wherein, $R^1$ and $R^2$ are each independently hydrogen, hydroxy, or $C_1$-$C_{10}$ alkoxy;
n is an integer of 1 to 5; and
m is an integer of 1 to 5.

Hereinafter, the present invention is described in more detail.

The present invention relates to a complex comprising a compound of formula (I), or a plant extract comprising the compound or a fraction thereof; and stevioside, or a plant extract comprising the stevioside or a fraction thereof:

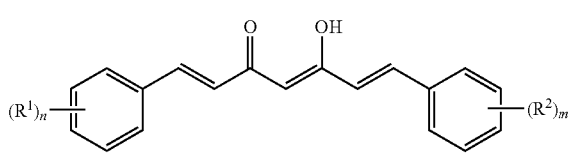

(I)

wherein, $R^1$ and $R^2$ are each independently hydrogen, hydroxy, or $C_1$-$C_{10}$ alkoxy;
n is an integer of 1 to 5; and
m is an integer of 1 to 5.

The complex of the present invention is preferably a formulation obtained by mixing a compound of formula (I), or a plant extract comprising the compound or a fraction thereof with stevioside, or a plant extract comprising the stevioside or a fraction thereof in a solvent, and bringing the mixture into reaction in an operating electronic oven.

The reaction of the mixture in the operating electronic oven may be carried out twice or more, and the mixture may be further cooled after each reaction. Also, the mixture may be further subject to ultrasonication prior to reaction in the operating electronic oven.

The complex of the present invention may comprise a compound of formula (I) wherein $R^1$ is independent on $R^2$ and hydrogen, hydroxy, or $C_1$-$C_{10}$ alkoxy; and $R^2$ is independent on $R^1$ and hydrogen, hydroxyl, or $C_1$-$C_{10}$ alkoxy. Also, in the compound of formula (I), when n is an integer of 2 or more (i.e, n≥2), two or more $R^1$ may be independently hydrogen, hydroxy, or $C_1$-$C_{10}$ alkoxy, and also, when m is an integer of 2 or more (i.e, m≥2), two or more $R^2$ may be independently hydrogen, hydroxy, or $C_1$-$C_{10}$ alkoxy.

In the present invention, the compound of formula (I) may be selected from a compound represented by any one of formulas (II) to (IV) and a mixture thereof:

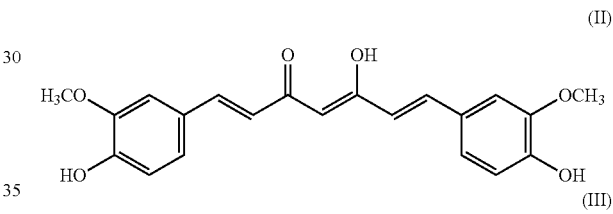

(II)

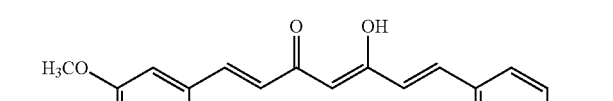

(III)

(IV)

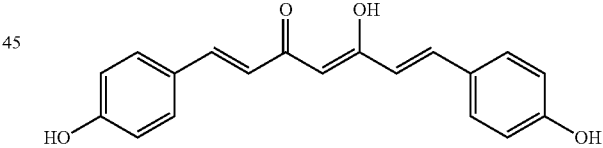

The compound of formula (I) is a curcuminoid-based compound, and examples thereof include curcumin of formula (II), demethoxycurcumin of formula (III) and bisdemethoxycurcumin of formula (IV). Among these, a preferred compound is curcumin of formula (II). These compounds may be used by purchasing what is commercially available, or using what has been extracted from plants, such as a turmeric, collected or cultivated by nature.

Also, the compound of formula (I) may be used in the form of a pharmaceutically acceptable salt, preferably an acid addition salt formed with a pharmaceutically acceptable free acid. Exemplary acids which may be used in the formation of the acid addition salt include inorganic acids such as hydrochloric acid, nitric acid, phosphoric acid, sulfuric acid, hydrobromic acid, hydroiodic acid, nitrous acid and phosphorous acid; and non-toxic organic acids such as aliphatic monocarboxylate, aliphatic dicarboxylate, phenyl-substituted alkanoate, hydroxyalkanoate, hydroxyalkandioate, aromatic acids, and aliphatic and aromatic sulfonic acids. Examples of a pharmaceutically non-toxic salt may include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methybenzoate, dinitrobenzoate, hydroxybenzoate, methoxybenzoate, phthalate, terephthalte, benzene sulfonate, toluene sulfonate, chloro benzene sulfonate, xylene sulfonate, phenyl acetate, phenyl propionate, phenyl butyrate, citrate, lactate, ß-hydroxybutyrate, glycolate, malate, tartrate, methane sulfonate, propane sulfonate, naphthalene-1-sulfonate, naphthalene-2-sulfonate, and mandelate.

In the present invention, the acid addition salt may be prepared by a conventional method, for example, by dissolving the compound of formula (I) in an excessive amount of an aqueous acid solution, to which a water-miscible organic solvent such as methanol, ethanol, acetone and acetonitrile is added, thereby precipitating a salt.

Also, in the present invention, the compound of formula (I) may be used in the form of a pharmaceutically acceptable metal salt formed with a base. For example, an alkaline metal or alkaline earth metal salt may be prepared by dissolving the compound of formula (I) in an excess amount of an alkaline metal hydroxide or alkaline earth metal hydroxide solution, filtering the resulting solution to remove the compound that is not being dissolved, followed by evaporating and drying the filtrate. In a pharmaceutical aspect, suitable exemplary metals which may be used in the formation of the metal salt include sodium, potassium and calcium. Also, a silver salt corresponding to the metal salt may be obtained by reacting an alkaline metal or alkaline earth metal salt with a suitable silver salt (e.g., silver nitrate).

In the complex of the present invention, the plant extract comprising the compound of formula (I) is not limited to its kinds, and it is preferably an extract of plants of *Curcuma* sp., more preferably an extract of a turmeric.

Generally, the term "turmeric" refers to a tuberous root of *Curcuma longa* Linne as is or a tuberous root of *Curcuma longa* Linne steamed and dried after removing the periderm (the Korean Pharmacopoeia 9$^{th}$ Edition), and the term "tuberous root" also known as a storage root refers to a thickened root.

Meanwhile, a rhizome of a *Curcuma longa* Linne is called *Curcuma longa* Rhizoma (the Korean Pharmacopoeia 9$^{th}$ Edition), and the term "rhizome", also known as a rootstalk refers to a stem of a plant creeping underground like a root.

In the present invention, the term "turmeric" refers to a tuberous root of a plant of *Curcuma* sp. including, but not limited to, *Curcuma wenyujin* (Y. H. Chen et C. Ling), *Curcuma longa* Linne, *Curcuma longa* Salisb., *Curcuma zedoaria, Curcuma kwansiensis* (S. G. Lee et C. F. Liang), *Curcuma aeruginosa, Curcuma phaeocaulis* Val.(Zingiberaceae), and *Curcuma domestica*.

Among plants of *Curcuma* sp., *Curcuma longa* Linne comprises several curcuminoid-based compound in various sites thereof, as confirmed through the Examples of the present invention. That is, as a result of extracting various sites of *Curcuma longa* Linne and measuring each extract for its content of a curcumin derivative, an ethanol extract of the tuberous root of *Curcuma longa* Linne was confirmed to have 17.0 g/kg of curcumin, 5.3 g/kg of demethoxycurcumin, and 3.4 g/kg of bisdemethoxycurcumin, while these compounds were not detected in an ethanol extract of the stem. Also, 2.8 g/kg of curcumin, 0.4 g/kg of demethoxycurcumin, and 6.8 g/kg of bisdemethoxycurcumin were detected in an ethanol extract of the rhizome of *Curcuma longa* Linne (Example 3).

In the present invention, the turmeric or *curcuma* may be obtained by purchasing what is commercially available, or what has been collected and cultivated by nature.

The turmeric extract may be prepared by conventional extracting methods known in the art, including ultrasonic extraction, filtration and reflux extraction. Preferably, it may be prepared by washing and drying a turmeric root to remove impurities, milling the turmeric root, and extracting the milled turmeric root with a solvent such as water, $C_1$-$C_4$ alcohol, or a mixture thereof, more preferably $C_1$-$C_4$ alcohol, most preferably methanol or ethanol. In the extraction, the amount of the solvent used may be two to twenty times of the dry weight of the turmeric. For example, an alcohol extract may be obtained by cutting the dried turmeric finely, putting it in an extract container, adding a solvent such as a lower $C_1$-$C_4$ alcohol or a mixture thereof, preferably methanol or ethanol to the container, and placing the container at room temperature for a predetermined time, followed by filtering. It is preferable to leave the extract at room temperature for preferably a week, and a concentration or freeze-drying procedure may be further carried out.

Meanwhile, in the present invention, a fraction of the plant extract comprising the compound of formula (I) may be obtained by fractionating the plant extract of the curcuminoid-based compound as defined above, preferably an extract of plants of *Curcuma* sp., more preferably an extract of a turmeric. More specifically, the turmeric extract may be suspended in water and fractionated with each of hexane and ethyl acetate to obtain a hexane fraction, an ethyl acetate fraction and a water fraction thereof.

In the complex of the present invention, the stevioside is a natural polysaccharide which is about 300 times sweeter than sucrose and consists of various glycosides including stevioside A1, A2, steviol 1, 2,3, dulcoside, rebaudioside a, b, c, e, f. This compound does not induce glycemic response and obesity, and can inhibit cavities.

In the present invention, the stevioside may be used by purchasing what is commercially available, or may be used by extracting from the stevia plant collected or cultivated by nature. The extraction of the stevia plant may be carried out by a conventional method.

Also, in the present invention, the stevioside is obtained from *Stevia rebaudiana* Bertoni, more preferably from the leaves thereof, but is not limited thereto.

In the present invention, the stevioside is used as is, or a dried form or a steamed and dried form thereof may be used. Also, the dried form may be used after milling into powders.

In the complex of the present invention, a plant extract comprising the stevioside is not limited to its kinds, but it is preferably an extract of the stevia plant.

The stevia is a genus of herbaceous perennials in the dicotyledon chrysanthemum family, native to the border stream wetland areas of South America including Paraguay, Argentina and Brazil, and has been used in herb tea, beverage, herbal medicine, natural sweetener, product for diabetes, diets and health supplements.

In the present invention, the stevia may be used by purchasing what is commercially available, or may be used by extracting from the stevia plant collected or cultivated by nature.

In the present invention, the leaves of the stevia are preferably used, but are not limited thereto.

In the present invention, an extract of the stevia may be obtained by extracting with water, a $C_1$-$C_4$ lower alcohol or a mixture thereof. Specifically, the stevia extract may be obtained by continuous extractions of 2 or 3 times, for example by agitating extraction and ultrasonic extraction using water or a lower alcohol such as methanol and ethanol, preferably ethanol, in an amount ranging about 2 to 10 times, preferably 2 to 5 times of the weight of the stevia, at a temperature of 20 to 50° C., preferably 25 to 30° C., followed by hot water extraction at 100° C., and filtering the resulting solution with a filter paper, concentrating the filtrate under a reduced pressure through a rotary concentrator, and freeze-drying and hot-air drying the residual under vacuum.

Also, the stevia extract of the present invention may comprise at least one selected from an extract obtained from extraction, a dilution or a concentration of the extract, a dried product obtained by drying the extract, and a product obtained from a crude purification or a purification thereof.

A fraction of the plant extract comprising the stevioside may be obtained by fractionating the plant extract.

When the turmeric extract is used as a plant extract comprising the compound of formula (I), the mixing ratio of the turmeric extract and the stevia extract may be optionally selected, and the turmeric extract and the stevia extract are preferably mixed in a ratio of 1:100 to 100:1, more preferably 1:10 to 10:1, most preferably 1:2 to 2:1.

In the present invention, when the turmeric extract is mixed with the stevioside, the mixing ratio thereof may be optionally selected, and the turmeric extract and the stevioside are preferably mixed in a ratio of 1:1000 to 1000:1, more preferably 1:100 to 100:1, most preferably 1:10 to 10:1.

In the present invention, when the compound of formula (I) is mixed with the stevia extract or the stevioside, the mixing ratio thereof may be optionally selected, and a preferred mixing ratio ranges from 1:10 to 1:30.

As another aspect, the present invention provides a pharmaceutical composition for preventing or treating an influenza virus infection comprising the complex as an active ingredient.

The term "prevent" used herein refers to all activities which inhibit the influenza virus infection or retard the pathogenesis of the influenza virus infection by administering the composition.

The term "treat" used herein refers to all activities which improve or favorably change the symptoms of the influenza virus infection by administering the composition. The influenza virus may be H1N1 influenza virus or H9N2 influenza virus, but is not limited thereto. Also, the influenza virus may cause influenza, cold, laryngopharyngitis, bronchitis, pneumonia, and particularly, bird flu, swine flu, or goat flu.

The composition of the present invention, which comprises the compound of formula (I), or a plant extract comprising the compound or a fraction thereof; and the stevioside, or a plant extract comprising the stevioside or a fraction thereof, is characterized by exhibiting an effect of inhibiting an activity of an influenza virus or inhibiting cell degradation against an influenza virus more superior than compared with the cases in which the compound of formula (I), or a plant extract comprising the compound or a fraction thereof is used alone, or the stevioside, or a plant extract comprising the stevioside or a fraction thereof is used alone.

In one example of the present invention in which specific pathogens free (SPF) chickens are inoculated with an influenza virus (H9N2), and a mixture of a compound of formula (II) and stevioside is orally administered therein 4 hours before the inoculation to 5 days after the inoculation, the groups treated with the mixture exhibited a surprising decrease in terms of a degree of virus re-isolation and a mean virus titer in the chickens' trachea, and cecal tonsil, as compared with the groups orally administered with only the compound of formula (II), the groups orally administered with only the ethanol extract of the turmeric, the groups orally administered with only the stevioside, and the groups with no treatment. As can be confirmed from these results, the composition of the present invention which comprises a mixture of a compound of formula (I) or a turmeric extract and a stevia extract or stevioside can more effectively inhibit an activity of an influenza virus, as compared with the cases in which each of the compound of formula (I), the turmeric extract comprising the compound, the stevia extract and the stevioside is used alone.

Also, the addition of the stevioside according to the present invention exhibited a surprising decrease in a degree of virus re-isolation and a mean virus titer even if curcumin is used in a small amount of 0.3 mg/kg/day, as compared with the case of when curcumin is used in an amount of 1 mg/kg/day. Thus, in accordance with the present invention, an influenza virus infection can be treated even by using just a small amount of curcumin.

Particularly, in the groups orally administered with only curcumine or an ethanol extract of the turmeric, a degree of virus re-isolation and a mean virus titer became decreased in only trachea, while there is no substantial decrease of a degree of virus re-isolation and a mean virus titer in cecal tonsil, as compared with the challenge control groups inoculated. Thus, the composition of the present invention can maintain good antiviral effect in the whole body of the subject infected with a virus.

In addition, the composition of the present invention may comprise a pharmaceutically acceptable carrier. The composition comprising the pharmaceutically acceptable carrier may be variously formulated for oral or parenteral administration. For formulation, a diluent or an excipient such as a filler, a bulking agent, a binder, a wetting agent, a desintegrant, a surfactant, and the like may be generally added. A solid formulation for oral administration may be used as a tablet, a pellet, powder, a granule, a capsule, and the like, and may be obtained by mixing at least one compound with at least one excipient, for example, starch, calcium carbonate, sucrose or lactose, gelatine, and the like. Besides a simple excipient, a lubricant such as magnesium stearate or talc may be used. A liquid formulation for oral administration may be used as a suspension, a solution, an emulsion, a syrup, and the like, and may include a common diluent such as water or liquid paraffin, as well as a variety of excipients, for example, a wetting agent, a sweetener, a flavoring agent, a preservative, and the like. A formulation for parenteral administration may be used as a sterilized aqueous solution, a non-aqueous solvent, a suspension, an emulsion, a lyophilized preparation, a suppository, and the like. As a non-aqueous solvent or a suspending agent, propylene glycol, polyethylene glycol, plant oils such as olive oil, or injectable ester such as ethyl oleate may be used. As a suppository base, witepsol, macrogol, TWEEN® 61, cacao butter, laurinum, or glycerolgelatin may be used.

The pharmaceutical composition may be formulated as at least one selected from a tablet, a pellet, powder, a granule, a capsule, a suspension, a liquid, an emulsion, a syrup, a sterilized aqueous solution, a non-aqueous solvent, a lyophilized preparation, and a suppositorie.

The composition of the present invention may be administered in a pharmaceutically effective dosage. The term "pharmaceutical effective dosage" used herein refers to an amount sufficient to treat a disease at a reasonable benefit/danger ratio within the range applicable to a medical treatment, and an effective dosage level may be determined based on the type, disease severity, age, and gender of individual, type of infected virus, drug efficacy, sensitivity to medication, time and route of administration, ration of excretion, period of treatment, drug combination, and factors well known in the medical field. However, for preferable effects, a dosage of the turmeric extract or its fraction according to the present invention may be 0.0001 to 100 mg/kg/day, preferably 0.001 to 100 mg/kg/day, and a dosage of the compound represented by chemical formula (I) may be 0.0001 to 100 mg/kg/day, preferably 0.001 to 10 mg/kg/day. The composition of the present invention may be administered alone or in combination with drugs, and may be administered sequentially or simultaneously with conventional drugs. Also, the composition may be administered in a single or multiple dose. Taking all the above factors into consideration, it is important to administer such a dosage as to obtain a maximum effect with a minimum amount without side effects, and the dosage may be easily determined by a person having an ordinary skill in the art.

As can be confirmed from one example of the present invention in which the pharmaceutical composition is orally administered in a chicken, a virucidal and antiviral effect can be maintained in cecal tonsil, as well as trachea. Therefore, it is preferred that the composition of the present invention be orally administered.

The composition of the present invention may be used alone or in combination with operation, endocrinotherapy, drug treatment, and methods using a biological response modifier, thereby preventing and treating an influenza virus infection.

Further, as yet another aspect, the present invention provides a food composition for preventing or improving an influenza virus infection, comprising the complex as an active ingredient. The compound of formula (I), or a plant extract comprising the compound or a fraction thereof; and stevioside, or a plant extract comprising the stevioside or a fraction thereof may be added to a food composition for the purpose of preventing or improving an influenza virus infection. When such components are used as a food additive, the extract, fraction, or compound may be used as is or may be used together with foods or food ingredients, and may be properly used by a conventional method. A mix ratio of active ingredients may be suitably determined depending on the purpose of use, for example, disease prevention or therapeutic treatment.

The food is not particularly limited to its kinds. Examples of the food comprising such a substance may include meats, sausages, breads, chocolates, candies, snacks, cookies, pizza, ramen, noodles, gums, dairy products including ice creams, various soups, beverages, teas, health drinks, alcoholic beverages, vitamin complexes, and the like, and may include all traditional health foods.

The health beverage composition of the present invention may additionally contain a flavoring agent or natural carbohydrate, like a general beverage. The natural carbohydrate may be monosaccharide such as glucose and fructose, disaccharide such as maltose and sucrose, polysaccharide such as dextrin and cyclodextrin, or sugar alcohol such as xylitol, sorbitol and erythritol. The sweetener may be a natural sweetener such as thaumatin and a stevia extract, or a synthetic sweetener such as saccharin and aspartame. The content of the natural carbohydrate may be generally about 0.01 to 0.04 g, preferably about 0.02 to 0.03 g, based on 100 ml of the composition of the present invention.

In addition to the above, the composition of the present invention may contain a variety of additives, for example, nutrient, vitamin, electrolyte, a flavoring agent, a coloring agent, pectic acid and its salt, alginic acid and its salt, organic acid, a protective colloid thickening agent, a pH adjusting agent, a stabilizer, a preservative, glycerin, alcohol, a carbonating agent for carbonated beverages, and the like. The content of the additive is not particularly important, but may be generally selected within the range of 0.01 to 0.1 parts by weights based on 100 parts by weight of the composition of the present invention.

Further, the composition of the present invention may contain a fruit pulp for the preparation of a natural fruit juice, fruit beverage and vegetable beverage. The content of the fruit pulp is not particularly important, but may be generally selected within the range of 0.01 to 0.1 parts by weights based on 100 parts by weight of the composition of the present invention. Such components may be used alone or in a mixture thereof.

As yet another aspect, the present invention provides a virucidal quasi-drug composition, comprising the complex as an active ingredient. When the compound of formula (I), or a plant extract comprising the compound or a fraction thereof; and stevioside, or a plant extract comprising the stevioside or a fraction thereof are used as an additive for quasi-drug products, the extract, fraction, or compound may be used as is or may be used together with foods or food ingredients, and may be properly used by a conventional method. A mix ratio of active ingredients may be suitably determined depending on the purpose of use, for example, disease prevention or therapeutic treatment.

Preferably, the quasi-drug composition may be used in manufacturing a natural disinfectant, a feed additive, a disinfectant cleaner, a shower foam, a mouthwash, a wet tissue, a detergent soap, a hand-wash, a humidifier filler, a mask, an ointment, a filter filler, and the like.

As yet another aspect, the present invention provides a feed additive for preventing or improving an influenza virus infection or a virucidal feed additive, which comprises the complex as an active ingredient.

Since the feed additive has a virucidal or antiviral efficacy, the feed additive can be steadily fed to poultry or livestock, thereby preventing viral diseases or improving viral diseases induced. The feed additive may be variously divided depending on the nutritional value, the main ingredient, the distribution, the moisture content, the combination conditions, and the finished form. Examples of a usable feed additive may include coarse feeds, concentrated feeds, supplement feeds, protein feeds, starch feeds, fatty feeds, and fibrous feeds, but are not limited thereto.

Also, the feed additive may further comprise a carrier acceptable in poultry or livestock. In the present invention, the feed additive may be used alone or in combination with a conventional carrier or a stabilizer, and if necessary, various component such as vitamins, amino acids and minerals, an antioxidant, an antibiotic agent, an antimicrobial agent and other additives. In addition, the feed additive may be suitably in the form of powders, granules, pellets and a suspension. The feed additive of the present invention may be fed to poultry or livestock by itself or by being added to a feed.

As yet another aspect, the present invention provides a feed comprising the feed additive. The above-mentioned feed additive may be used as a raw material or additive of a feed or potable water for various animals, and it may be used in a feed composition.

As still yet another aspect, the present invention provides a method for treating an influenza virus infection, comprising administering the complex to an individual. The complex which comprises a compound of formula (I), or a plant extract comprising the compound or a fraction thereof; and stevioside, or a plant extract comprising the stevioside or a fraction thereof can be administered to an individual infected or to be infected with influenza virus, thereby treating an influenza virus infection.

The influenza virus is preferably H1N1 influenza virus or H9N2 influenza virus, but is not limited thereto. The disease caused by influenza virus infection may be influenza, cold, laryngopharyngitis, bronchitis, pneumonia, and particularly, bird flu, swine flu, or goat flu.

The term "individual" used herein refers to all animals including humans infected or to be infected with influenza virus, and the disease may be effectively prevented and treated by administering the complex of the present invention to the individual. For example, the complex of the present invention may treat chickens or swines infected with avian influenza virus of a variety of influenza virus subtypes or variants. The complex of the present invention may be administered in combination with a conventional drug used for a disease caused by influenza virus infection.

The complex of the present invention may be administered via any general route as long as the composition can be delivered to a target tissue. The complex of the present invention may be administered by an intraperitoneal, intravenous, intramuscular, subcutaneous, intradermal, oral, intranasal, intralung, or rectal route of administration depending on the intent of administration, but the present invention is not limited thereto. Also, the complex may be administered using any device capable of delivering an active ingredient to a target cell.

As can be confirmed from one example of the present invention in which the pharmaceutical composition is orally administered in a chicken, a virucidal and antiviral effect can be maintained in the cecal tonsil as well as trachea. Therefore, it is preferred that the composition of the present invention is orally administered.

The composition of the present invention, which comprises the compound of formula (I), or a plant extract comprising the compound or a fraction thereof; and the stevioside, or a plant extract comprising the stevioside or a fraction thereof, is characterized by exhibiting an effect of inhibiting an activity of an influenza virus or inhibiting cell degradation against an influenza virus far more superior than the cases in which the compound of formula (I), or a plant extract comprising the compound or a fraction thereof is used alone, or the stevioside, or a plant extract comprising the stevioside or a fraction thereof is used alone.

Particularly, the composition of the present invention, which comprises the compound of formula (I), or a plant extract comprising the compound or a fraction thereof; and the stevioside, or a plant extract comprising the stevioside or a fraction thereof, is characterized by exhibiting a surprising decrease in terms of a degree of virus re-isolation and a mean virus titer in the chickens' trachea, and cecal tonsil, as compared with the challenge positive control groups inoculated, the groups administered with the compound of formula (I), the groups administered with a plant extract comprising the compound of formula (I), the groups administered with a stevia extract (Experimental Example 3). That is, the complex of the present invention exhibits an antiviral effect against viruses present in trachea, as well as cecal tonsil which is the end of internal organs, and therefore, it can maintain an antiviral activity in the whole body of an individual infected with a virus.

Advantageous Effects

According to the present invention, the complex comprising a compound of formula (I), or a plant extract comprising the compound or a fraction thereof; and stevioside, or a plant extract comprising the stevioside or a fraction thereof can be used as the active ingredient of a pharmaceutical composition for preventing or treating an influenza virus infection, a food composition for preventing or improving an influenza virus infection, a virucidal quasi-drug composition, a virucidal feed additive composition. Particularly, the composition of the present invention, which is obtained by mixing the compound of formula (I), or a plant extract comprising the compound or a fraction thereof; and stevioside, or a plant extract comprising the stevioside or a fraction thereof, can increase a virucidal effect and an effect of inhibiting cell degradation against an influenza virus as well as antiviral activity, and thus can be usefully used in the prevention and treatment of an influenza virus infection, and can maintain an antiviral activity in the whole body of an individual infected with a virus.

BEST MODE

Hereinafter, the present invention will be described in detail through examples and experimental examples. However, the description proposed herein is just a preferable example for the purpose of illustrations only, not intended to limit the scope of the invention, so it should be understood that the examples are provided for a more definite explanation to an ordinary person skilled in the art.

EXAMPLE 1

Preparation of Turmeric Extract

A turmeric used in this example is generally available in a medicinal herb shop or market. The steamed and dried radix of *Curcuma longa* Linne was purchased, and to effectively obtain an extract of the present invention, was milled in powder form. 1.6 kg of turmeric was dissolved in 7.5 l of 100% ethanol (EtOH), placed at room temperature for 5 days, and filtered through a filter paper and concentrated, to obtain 170 g of a turmeric ethanol extract.

EXAMPLE 2

Separation and Purification of Turmeric Fraction and Curcuminoid-based Compound from Turmeric Extract 170 g of the turmeric ethanol extract obtained in example 1 was suspended in 1 l of water. The suspension was put in a separatory funnel, and fractionally extracted with n-hexane and ethylacetate in sequence, to yield 23 g of an n-hexane soluble extract, 85 g of an ethylacetate soluble extract, and 34 g of a water soluble extract.

85 g of the obtained ethylacetate soluble extract was separated into 15 fractions Fr.-1 to Fr.-15 by silica gel column chromatography (500 g silica gel, mesh 70~230) using solvents of chloroform, methanol, and mixture thereof (80:1~1:1) as mobile phases. Among them, 16 g of the sixth fraction Fr.-6 was separated into 5 fractions Fr.-6-1 to Fr.-6-5 by silica gel column chromatography (30 g, mesh 230~400) using a mixed solvent of n-hexane and ethylacetate (20:1~1:1 (v/v)) as a mobile phase.

After performing silica gel column chromatography on Fr.-6-2 and Fr.-6-3 fractions (11 g) using solvents of chloroform, methanol, and mixture thereof (80:1~4:1) as mobile phases, a fraction obtained was developed by preparative TLC using a mixed solvent of n-hexane and ethylacetate (4:1 (v/v)) as a mobile phase, to yield 8 g of a pure compound 1. Also, 14 g of the eighth fraction Fr.-8 was repetitively separated by silica gel column chromatography (30 g, mesh 230~400) using a mixed solvent of n-hexane and ethylacetate (20:1~1:1 (v/v)) and a mixed solvent of chloroform and methanol (80:1~20:1 (v/v)) as mobile phases, to yield 0.4 g of a compound 2 and 0.2 g of a compound 3.

EXAMPLE 3

Structural Analysis of Curcuminoid-based Compound

The molecular weight and molecular formula of the curcuminoid-based compounds obtained in Example 2 was confirmed using a VG high resolution GC/MS spectrometer (Election Ionization MS, Autospec-Ultima). Also, the molecular structure was confirmed through nuclear magnetic resonance analysis (Bruker AM500) using $^1$H-NMR, $^{13}$C-NMR, and 2D NMR spectroscopy materials.

Based on comparing the above results with those of published papers, curcumin, demethoxycurcumin and bisdemethoxycurcumin represented by formulas (I) to (IV) were identified (*Food Chem.* 265-272, 2009; *J. Nat. Prod.* 1227-1231, 2002; *J. Nat. Prod.* 1531-1534, 1998; *J. Agric. Food Chem.* 3668-3672, 2002). The analysis results are shown below.

Compound 1: Curcumin (II)

1) Property: light orange powder (m.p. 183° C.)
2) Molecular weight: 368.3
3) Molecular formula: $C_{21}H_{20}O_6$
4) $^1$H-NMR (acetone-$d_6$, 500 MHz) δ 7.62 (2H, d, J=15.80 Hz, H-4, H-4'), 7.35 (2H, d, J=1.91 Hz, H-6, H-6'), 6.83 (2H, H-3, H-5), 7.20 (2H, dd, J=8.3, 1.9 Hz, H-10, H-10'), 6.90 (2H, d, J=8.15 Hz, H-9, H-6'), 5.99 (1H, s, H-1), $^{13}$C-NMR (acetone-$d_6$, 125 MHz) δ 56.72, 102.01, 111.95, 116.64, 122.72, 124.25, 128.58, 141.81, 149.20, 150.44, 184.94.

Compound 2: Demethoxycurcumin (III)

1) Property: orange powder (m.p. 220° C.)
2) Molecular weight: 338
3) Molecular formula: $C_{20}H_{18}O_5$
4) $^1$H-NMR (acetone-$d_6$, 500 MHz) δ 7.62-7.55 (4H), 7.34 (1H), 7.18 (1H), 6.89 (3H), 6.70 (2H), 5.97 (1H), $^{13}$C-NMR (acetone-$d_6$, 125 MHz) δ 56.38, 101.79, 111.53, 116.30, 116.89, 122.12, 122.35, 123.98, 127.77, 128.24, 131.06, 141.13, 141.48, 148.87, 150.13, 160.64, 184, 66.

Compound 3: Bisdemethoxycurcumin (IV)

1) Property: orange powder (m.p. 224° C.)
2) Molecular weight: 308
3) Molecular formula: $C_{19}H_{16}O_4$
4) $^1$H-NMR (acetone-$d_6$, 500 MHz) δ 7.62-7.56 (6H), 6.91-6.87 (4H), 6.68-6.65 (2H), 5.98 (1H), $^{13}$C-NMR (acetone-$d_6$, 125 MHz) δ 101.82, 116.87, 122.11, 127.79, 131.06, 141.12, 160.58, 184, 62.

EXPERIMENTAL EXAMPLE 1

Determination of Neuraminidase A/Bervig_Mission/1/18 (rvH1N1) Inhibitory Activity of Turmeric Extract, Fraction, and Curcuminoid-Based Compound To determine the neuraminidase inhibitory activity of the turmeric extract, the turmeric fraction, and the curcuminoid-based compounds separated therefrom that were obtained in Examples 1 and 2 of the present invention, neuraminidase (R&D SYSTEM, 4858-NM) of a recombinant rvH1N1 influenza A virus of 1918 Spanish flu virus (A/Bervig_Mission/1/18) was used. 2'-(4-Trimethylumbelliferyl)-α-D-N-acetyl-neuraminic acid sodium salt from Sigma was used as a substrate.

The turmeric extract and its fraction of Examples 1 and 2 were dissolved in methanol. As a substrate, 2'-(4-trimethylumbelliferyl)-α-D-N-acetyl-neuraminic acid sodium salt (final concentration 200 μM) was added to 20 μL of each solution. The result was mixed with 80 μL of a tris buffer (pH 7.5) containing 5 mM $CaCl_2$ and 200 mM NaCl, and reacted with 50 μL of neuraminidase (final enzyme concentration 0.05 ng/μL) as a zymogen at 25° C. for 10 minutes.

The neuraminidase inhibitory activity was determined by measuring absorbance at 365 nm and emittance at 445 nm using a fluorescence spectroscope.

The measurement results are shown in Table 1 below.

TABLE 1

| Substance | Neuraminidase inhibitory activity($IC_{50}$)[1]<br>A/Bervig-Mission/1/18(rvH1N1) |
|---|---|
| Turmeric ethanol extract | 3.1 μg/mL |
| Turmeric hexane fraction | 262.0 μg/mL |
| Turmeric ethylacetate fraction | 0.9 μg/mL |
| Turmeric water fraction | 61.5 μg/mL |
| Curcumin | 3.0 μM |
| Demethoxycurcumin | 3.0 μM |
| Bisdemethoxycurcumin | 6.0 μM |

[Note]
[1] a result value is an average of two tests.

As can be seen in Table 1 showing the determination results of neuraminidase inhibitory activity of each of the turmeric extract, fraction, and curcuminoid-based compounds according to the present invention, the turmeric ethanol extract had an $IC_{50}$ value of 3.1 μg/mL against influenza virus neuraminidase, the turmeric hexane fraction had an $IC_{50}$ value of 262.0 μg/mL, the turmeric ethylacetate fraction had an $IC_{50}$ value of 0.9 μg/mL, the turmeric water fraction had an $IC_{50}$ value of 61.5 μg/mL, curcumin and demethoxycurcumin had each an $IC_{50}$ value of 3.0 μM, and bisdemethoxycurcumin had an $IC_{50}$ value of 6.0 μM. Accordingly, it was determined through the above results that the turmeric extract, its fraction, and curcuminoid-based compounds according to the present invention had excellent neuraminidase inhibitory activity.

EXPERIMENTAL EXAMPLE 2

Determination of Influenza Virus Inhibitory Activity of Curcuminoid-based Compound Separated from Turmeric Extract, Ethylacetate Fraction, and Ethanol Extract To determine the antiviral effects of the curcuminoid-based compounds, ethylacetate fraction, and ethanol extract separated from the turmeric extract on influenza virus H1N1 (A/PR/8/34) and H9N2 (A/Chicken/Korea/MS96/96), a test below was carried out in vitro using a Madin-Darby canine kidney (MDCK, ATCC CCL-34) cell of a dog.

First, MDCK cells were put in a 96-well microplate at a density of $1 \times 10^5$/well, and incubated in a culture medium (EMEM) containing 100 units penicillin, 100 μg streptomycin and 10% FBS. When the MDCK cells are grown as a monolayer, the MDCK cells were washed twice with a culture medium (EMEM) only containing antibiotic. Each of H1N1 and H9N2 strains was diluted with 100 $TCID_{50}$, and put in an EP tube. The curcuminoid-based compounds, ethylacetate fraction and ethanol extract separated from the turmeric extract diluted with dimethylsulfoxide (DMSO) were put in each tube based on concentration, followed by reaction at 4° C. for 1 hour. After the lapse of 1 hour, the reacted solutions were inoculated into 3 wells of the pre-washed MDCK cells at each concentration, followed by incubation at 35° C. for 1 hour (hereinafter, referred to as a test sample). Under the same conditions, non-infected+non-administered cells (MDCK cells not infected with an H1N1 or H9N2 strain and not administered with the curcuminoid-based compound) and infected+non-administered cells (MDCK cells infected with an H1N1 or H9N2 strain and not administered with curcumin), incubated at 35° C. for 1 hour, were each set as a control and a virus control. After the lapse of 1 hour, the culture mediums of the plate were all removed, and the cells were washed once with PBS. 100 ml of a culture medium (EMEM) containing antibiotic and 10 μg/mL trypsin was dispensed in each well of the cells, followed by incubation at 35° C. for 48 to 72 hours. The incubation was performed for 48 to 72 hours until the infected+non-administered cells (virus control) have cytopathic effects (CPE). The state of the cells was observed with an inverted microscope every day. After the cells were incubated for 48 to 72 hours, 10 Ml of a cell counting kit-8 (Dojin, Kumanoto, Japan, tetrazolium salt WST-8) was added to each well to determine the cell survival, followed by reaction at 35° C. for 2 hours, and the absorbance was measured at 450 nm. In this instance, the antiviral effects (Inhibition (%)) of the curcuminoid-based compounds, ethylacetate fraction, and ethanol extract separated from the turmeric extract of the present invention were calculated using the following mathematical formula (I) in comparison with the non-infected+non-administered cells (control) and the infected+non-administered cells (virus control). The results are shown in Table 2 below.

$$\text{Inhibition}(\%) = \frac{OD \text{ value of test sample} - OD \text{ value of infected} + \text{non-administered control}}{OD \text{ value of non-infected} + \text{non-administered control} - OD \text{ value of infected} + \text{administered control}} \times 100 \quad \text{Equation (I)}$$

wherein, the OD value is absorbance measured at 450 nm.

Meanwhile, to determine the cell degeneration inhibitory effects of the curcuminoid-based compounds, ethylacetate fraction, and ethanol extract separated from the turmeric extract on influenza virus H1N1 (A/PR/8/34) and H9N2 (A/Chicken/Korea/MS96/96), MDCK cells were washed twice with a culture medium (EMEM) only containing antibiotic, inoculated with influenza virus (H1N1 or H9N2 strain), and incubated at 35° C. for 1 hour. After the lapse of 1 hour, the virus solution used in inoculation was completely removed, and the curcuminoid-based compounds, ethylacetate fraction, and ethanol extract separated from the turmeric extract were each inserted into the virus-inoculated MDCK cells. Subsequently, the cell degeneration inhibitory effects (Inhibition (%)) of the curcuminoid-based compounds, ethylacetate fraction, and ethanol extract separated from the turmeric extract of the present invention were determined using the above Equation (I). The results are shown in Table 2 below.

TABLE 2

| Substance | H1N1 (A/PR/8/34) | | | H9N2 (A/Chicken/Korea/MS96/96) | | |
|---|---|---|---|---|---|---|
| | $CC_{50}$ (μM)[a] | $EC_{50}$ (μM)[b] | SI[c] | $CC_{50}$ (μM)[a] | $EC_{50}$ (μM)[b] | SI[c] |
| Virucidal effect | | | | | | |
| Tamiflu | >200 | 18.5 | >10.8 | >200 | <1 | >200 |
| Curcumin | 94.1 | 7.1 | 13.3 | 94.1 | 18.6 | 5.1 |
| Demethoxycurcumin | 97.0 | 8.0 | 23.1 | 97.0 | 18.2 | 5.3 |
| Bisdemethoxycurcumin | >200 | 28.1 | >7.1 | >200 | >200 | <1 |
| Ethylacetate fraction | 82.1 μg/mL | 9.0 μg/mL | 9.1 | 82.1 μg/mL | 20.0 μg/mL | 4.1 |
| Ethanol extract | 55.7 μg/mL | 8.7 μg/mL | 6.4 | 55.7 μg/mL | 30.4 μg/mL | 1.8 |
| Cell degeneration inhibitory effect | | | | | | |
| Tamiflu | >200 | 3.0 | >66.7 | >200 | <1 | >200 |
| Curcumin | 94.1 | 40.7 | 2.3 | 94.1 | 10.9 | 8.6 |
| Demethoxycurcumin | 97.0 | 60.8 | 1.6 | 97.0 | 24.9 | 3.9 |
| Bisdemethoxycurcumin | >200 | 141.5 | >1.4 | >200 | 181.6 | >1.1 |
| Ethylacetate fraction | 82.1 μg/mL | 23.5 μg/mL | 3.5 | 82.1 μg/mL | 11.6 μg/mL | 7.1 |
| Ethanol extract | 55.7 μg/mL | 27.8 μg/mL | 2.0 | 55.7 μg/mL | 31.5 μg/mL | 1.8 |

[Note]
[a]$CC_{50}$, 50% cytotoxic concentration
[b]$EC_{50}$, 50% antiviral concentration
[c]SI, selective index, $CC_{50}/EC_{50}$ a. The curcuminoid-based compounds, ethylacetate fraction and ethanol extract were each mixed with virus, followed by reaction at 4° C. for 1 hour, and MDCK cells were infected with the virus. After the lapse of 1 hour, the cells were washed once with PBS and a culture medium (EMEM) containing 10 mg/mL trypsin was dispensed. The cells were incubated at 35° C. for 48 to 72 hours.

b. After 1 hour of the virus infection, the medium including the virus was removed and replaced with a fresh medium containing each of the curcuminoid-based compounds, ethylacetate fraction, and ethanol extract, and then the cells were incubated for 48 to 72 hours.

c. A value of $CC_{50}/EC_{50}$ as selective index (SI)

As shown in Table 2, the curcuminoid-based compounds had excellent virucidal effects on an H1N1 strain exhibiting a selective index (SI) of 13.3, 23.1, and greater than 7.1. Also, the curcuminoid-based compounds exhibited a selective index (SI) of 5.1, 5.3, and less than 1.0 against an H9N2 strain. Accordingly, it was determined that the curcuminoid-based compounds had virucidal effects on a variety of virus strains. The turmeric ethylacetate fraction and turmeric ethanol extract had excellent virucidal effects on an H1N1 strain, exhibiting a selective index (SI) of 9.1 and 6.4, respectively. According to the observation results of the cell morphology with an inverted microscope, it was found that MDCK cells inoculated with virus (H1N1 or H9N2) were almost degenerated, leading to 90 to 100% of cytopathic effects, while virus-infected MDCK cells treated with the curcuminoid-based compounds, ethylacetate fraction, and ethanol extract exhibited a similar aspect to a non-infected+non-administered control.

Furthermore, the curcuminoid-based compounds had cell degeneration inhibitory effects on H1N1 and H9N2. In particular, the curcuminoid-based compounds had excellent cell degeneration inhibitory effects on an H9N2 strain exhibiting a selective index (SI) of 8.6, 3.9, and greater than 1.1, and had cell degeneration inhibitory effects on an H1N1 strain exhibiting a selective index (SI) of 2.3, 1.6, and greater than 1.4. According to the observation results of the cell morphology with an inverted microscope, it was found that MDCK cells inoculated with virus (H1N1 or H9N2) were almost degenerated, leading to 90 to 100% of cytopathic effects, while virus-infected MDCK cells treated with the curcuminoid-based compounds, ethylacetate fraction, and ethanol extract exhibited a similar aspect to a non-infected+non-administered control.

Accordingly, the composition of the present invention has virucidal effects by directly working on the virus before the virus infects cells, and has excellent cell degeneration inhibitory effects by preventing the virus from releasing from cells through replication after the cells are infected with the virus, and thus can be useful in preventing and treating an influenza virus infection.

EXPERIMENTAL EXAMPLE 3

Determination of Antiviral Activity of the Complex According to the Present Invention Using SPF Chicken as an Animal Model To determine the antiviral activity of the complex of the present invention which comprises a compound of formula (I) having an antiviral activity as confirmed in the above Experimental Example, a turmeric extract comprising the compound, a fraction of the extract, and stevioside, the following test was performed.

First, curcumin was mixed with stevioside to obtain a complex. Specifically, 10 g/L of curcumin and 1 to 100 g/L of stevioside were well mixed and subject to ultrasonication at 70° C. for 30 minutes, and the sonicated mixture was brought into reaction in a 700W oven for 15 minutes, and cooled. The reaction for 15 minutes in the oven was further repeated 3 times.

As a result, the resulting solution had the maximum 3.5 g/L of curcumin in 100 g/L of the stevioside solution, and the resulting solution was used directly or after diluting depending on its uses. The complex prepared above was confirmed to provide curcumin in an amount of 0.3 mg/kg/day.

In order to confirm the antiviral and virucidal activity of the complex, 60 chickens of being specific pathogens free (SPF) and aged 3 weeks were grouped into the total six groups (10 chickens per a group), i.e., 3 test groups orally administered with curcumin, a turmeric extract, and a composition comprising a mixture of curcumin and stevioside, respectively; a test group orally administered with 10% stevioside; a challenge positive control group inoculated; and a negative control group (Table 3).

TABLE 3

| Group | Samples |
|---|---|
| 1 | Curcumin (1 mg/kg/day) |
| 2 | Turmeric ethanol extract (comprising 10% curcumin) |
| 3 | Composition of curcumin (1%) + stevioside (10%) (300 μL/dose) |
| 4 | Stevioside (10%) (300 μL/dose) |
| 5 | Challenge positive control group |
| 6 | Negative control group |

As a test virus, influenza virus type A (H9N2) was used and the listed samples were orally administered in an amount of $10^{6.0}$/100 μL/dose in each group e4 hours before the challenge inoculation of the virus to 5 days after the inoculation. After 5 days from the inoculation, a degree of inhibiting the inoculated virus proliferation was confirmed in the trachea and cecal tonsil of each group, and the results thereof are shown in Table 4.

TABLE 4

| Group | Number of inoculated chickens | Virus re-isolation[A] Trachea | Virus re-isolation[A] Cecal Tonsil | Mean virus titer($log_{10}EID_{50}/g$) Trachea | Mean virus titer($log_{10}EID_{50}/g$) Cecal Tosnil |
|---|---|---|---|---|---|
| G1 | 10 | 4/10 | 6/10 | 1.7 ± 2.5 | 4.2 ± 3.6 |
| G2 | 10 | 9/10 | 6/10 | 4.8 ± 1.56 | 4.20 ± 3.61 |
| G3 | 10 | 8/10 | 2/10 | 4.0 ± 2.17 | 1.40 ± 2.95* |
| G4 | 10 | 10/10 | 8/10 | 5.80 ± 1.3 | 5.30 ± 3.5 |
| G5 | 10 | 10/10 | 8/10 | 5.70 ± 1.9 | 5.40 ± 2.88 |
| G6 | 10 | 0/10 | 0/10 | 0.00 ± 0.0 | 0.00 ± 0.0 |

[A]Number of virus-positive chicken/Number of inoculated chickens,

*$P < 0.05$ by one-tailed t-test

As can be seen in Table 4, when the samples of the present invention were administered 4 hours before the challenge inoculation of the virus to 5 days after the inoculation to confirm their effect on the inhibition of an influenza virus proliferation, in the trachea and cecal tonsil of the groups orally administered with curcumin, a turmeric extract, and a composition comprising a mixture of curcumin and stevioside, respectively, a degree of virus re-isolation and a mean virus titer were substantially reduced as compared with the challenge positive control group and the negative control group.

Specifically, in the case of the group administered with curcumin, a degree of virus re-isolation and a mean virus titer were substantially reduced in the trachea, but were not surprisingly reduced in the cecal tonsil, as compared with the challenge positive control group. Also, in the case of the group administered with a turmeric ethanol extract comprising 10% curcumin, a degree of virus re-isolation and a mean virus titer were not surprisingly reduced in both trachea and cecal tonsil, as compared with the challenge positive control group. In contrast, in the case of the group administered with a composition comprising a mixture of curcumin and stevioside, a degree of virus re-isolation and a mean virus titer were surprisingly reduced in both trachea and cecal tonsil, as compared with the challenge positive control group, the group administered with curcumin, and the group administered with the turmeric extract.

From these results, it was confirmed that the composition comprising a mixture of curcumin and stevioside can exhibit antiviral effects against viruses present in trachea, as well as cecal tonsil which is the end of internal organs when it is administered in an animal model, and therefore, it can maintain an antiviral activity in the whole body of an individual infected with a virus.

EXPERIMENTAL EXAMPLE 4

Acute Toxicity Test of Compound of the Present Invention

To determine the acute toxicity of the compounds of the present invention, the following test was performed.

Specific pathogens free (SPF) C57BL/6J mice including 12 female and 12 male, aged 6 weeks (sample), were grouped into four groups (3 female mice and 3 male mice as a test group), and bred in an animal room under the conditions of a temperature of 22±3° C., a humidity of 55±10%, and an illumination strength of 12L/12D. Before the test, the mice were gone through domestication for 1 week. The mice were freely fed with laboratory animal feeds (feed for mice and rats, CJ Corporation in Seoul, Republic of Korea) and sterile water.

A sample was prepared by adding 0.5% of TWEEN®80 to each of the compounds of formulas (II) to (IV) obtained in Example 2 at a concentration of 50 mg/mL, and administered in a dosage of 0.04 mL (100 mg/kg), 0.2 mL (500 mg/kg), and 0.4 mL (1,000 mg/kg) per 20 g of the mouse weight. The sample was orally administered in a single dose, and after administration, side effect or survival was observed for 7 days. That is, on the day of administration, the general symptomatic change and survival were observed after 1 hour, 4 hours, 8 hours, and 12 hours of administration, and from the next day of administration to the seventh day, were observed once or more each in the forenoon and afternoon every day.

The acute toxicity test results showed that all the mice administered with the sample did not have a noteworthy clinical sign and there was no dead mouse. Also, the toxicity change was not observed in the weight change, blood test, biochemical examination of blood, and autopsy findings.

The curcuminoid-based compound used in the present invention is not subject to a toxicity change in all the mice until a dosage is 1,000 mg/kg, and it was confirmed that the compounds of the present invention are a stable substance having 1,000 mg/kg or more of an oral $LD_{50}$, that is, a minimum lethal dose. Also, the stevioside used in the present invention is a safe substance which has been conventionally used as a sweetener. Therefore, the composition of the present invention, which comprises the curcuminoid-based compound, or a plant extract comprising the compound or a fraction thereof; and stevioside, or a plant extract comprising the stevioside or a fraction thereof, can be safely and effectively used in the treatment of an influenza virus infection.

What is claimed is:

1. A method of treating a H9N2 influenza virus infection, comprising administering to an individual in need thereof a composition comprising therapeutically effective amounts of the compound of formula (I) and stevioside:

(I)

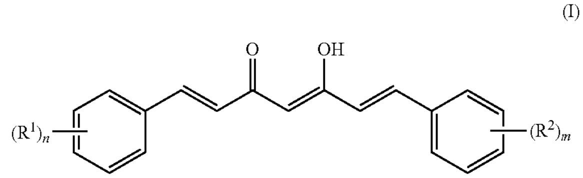

wherein, $R^1$ and $R^2$ are each independently hydrogen, hydroxy, or $C_1$-$C_{10}$ alkoxy;

n is an integer of 1 to 5; and m is an integer of 1 to 5.

2. The method of claim 1, wherein the composition is orally administered.

3. The method of claim 1, wherein the compound of formula (I) is obtained from turmeric extract, and the stevioside is obtained from *Stevia rebaudiana* Bertoni.

4. The method of claim 1, wherein the composition is formulated as at least one selected from a tablet, a pellet, powder, a granule, a capsule, a suspension, a liquid, an emulsion, a syrup, a sterilized aqueous solution, a non-aqueous solvent, a lyophilized preparation, and a suppository.

5. The method of claim 1, wherein the composition is a food.

* * * * *